United States Patent [19]

Galen et al.

[11] Patent Number: 5,085,224

[45] Date of Patent: Feb. 4, 1992

[54] PORTABLE SIGNALLING UNIT FOR AN EKG

[75] Inventors: Peter M. Galen; Susan R. Hart; William E. Saltzstein, all of McMinnville, Oreg.

[73] Assignee: Hewlett-Packard Company, Palo Alto, Calif.

[21] Appl. No.: 529,015

[22] Filed: May 25, 1990

[51] Int. Cl.⁵ .......................................... A61N 5/0402
[52] U.S. Cl. ........................................ 128/696; 128/903
[58] Field of Search ............... 128/695, 696, 709, 710, 128/712, 901, 902, 903, 904, 905

[56] References Cited

U.S. PATENT DOCUMENTS

| | | | |
|---|---|---|---|
| 3,199,508 | 8/1965 | Roth | 128/904 |
| 3,603,881 | 9/1971 | Thornton | 128/903 |
| 3,757,778 | 9/1973 | Graham | 128/2.06 R |
| 3,830,228 | 8/1974 | Foner | 128/696 |
| 3,905,364 | 9/1975 | Cudahy et al. | 128/696 |
| 4,027,663 | 6/1977 | Fischler et al. | 128/2.06 R |
| 4,173,221 | 11/1979 | McLaughlin et al. | 128/696 |
| 4,606,352 | 8/1986 | Geddes et al. | 128/712 |
| 4,794,532 | 12/1988 | Lechband | 128/709 |
| 4,883,064 | 11/1989 | Olson et al. | 128/696 |

*Primary Examiner*—William E. Kamm

[57] ABSTRACT

A portable leadwire signalling terminal is provided as an interface between an EKG base unit and a patient. The portable terminal includes a signal transceiver which transmits leadwire information to the EKG apparatus, as well as pushbutton information. The EKG unit sends back information suitable for a video display in the terminal. This information is indicative of noise on each leadwire, as well as whether a lead wire is disconnected.

11 Claims, 4 Drawing Sheets

PORTABLE SIGNALLING UNIT FOR AN EKG

TECHNICAL FIELD

The invention relates to electrical signalling apparatus for medical instruments and more particularly to a signalling unit for use in an EKG apparatus.

BACKGROUND ART

U.S. Pat. No. 3,757,778, M. Graham teaches that EKG leadwires may be terminated in a wire distribution head which is connected by means of a cable to an EKG. The head includes lamps which indicate the effectiveness of connection of an electrode between the head and the patient. The patent recognizes the need for terminating EKG leadwires which cannot conveniently extend all the way to an EKG apparatus. While the Graham apparatus is useful, there is a need for further information at the distribution head. Often an operator has the need to evaluate signal quality as received by the EKG apparatus. Moreover, an operator may have a need to signal the EKG apparatus from a position close to the patient. For example, such signalling may initiate EKG measurements or terminate them.

Accordingly, there is a need for means of communicating with an EKG host system in order to receive data from the host indicative of signal quality, as well as providing a means for controlling the host operation.

SUMMARY OF THE INVENTION

The above need has been met with a portable terminal block having wire contacts for terminating EKG leadwires from a subject connected to the leadwires. The terminal block houses a signal transceiver which can send and receive data to a remote EKG host. The transceiver includes a transmitter which receives data from the leadwire and includes the data for transmission in a bidirectional communications channel extending between the terminal block and the remote EKG. The transceiver also includes a receiver which can decode signals from the remote host. The remote host may indicate the amount of noise in a particular channel or whether a leadwire associated with the channel is connected to a patient. Such information is derived from a signal processor associated with the host EKG unit. The remote host may also give generalized feedback, such as the status of control functions initiated at the remote host.

The terminal block may further include a manual contact, such as button(s) or switch(es), which acts to telegraphically communicate with the host unit over the communications channel. The switch or button may be used to initiate or terminate EKG functioning. The terminal block is also provided with a video display having a plurality of adjacent cells, each suitable for displaying graphical or roughly numeric information relating to the condition of an EKG leadwire. Alphabetic and numeric character display is also possible.

The portable signalling unit of the present invention allows an operator to remain in the vicinity of a patient while controlling EKG apparatus functioning and observing the amount of noise in each of the leadwires associated with the terminal block. The operator may also observe feedback from the controlling EKG apparatus via the terminal block.

BEST MODE FOR CARRYING OUT THE INVENTION

Figure 1:
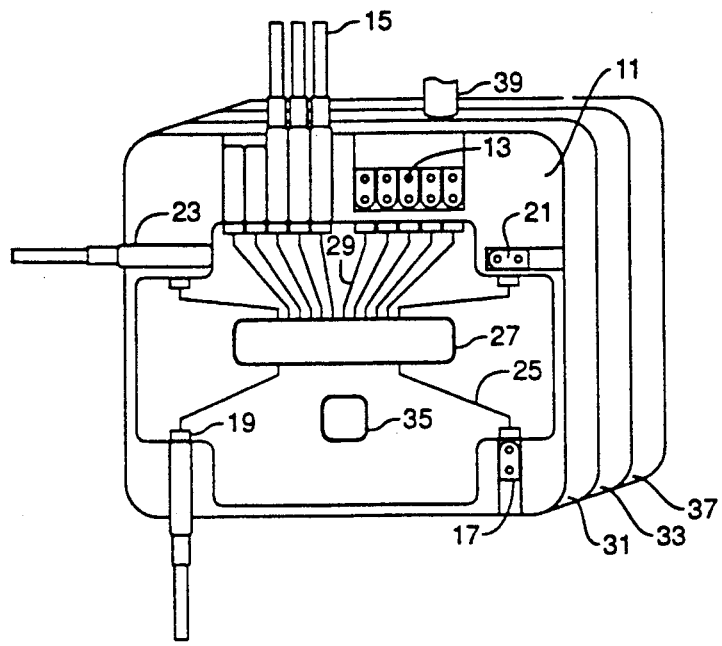
FIG. 1 is a perspective view of a portable signalling unit in accord with the present invention.

With reference to FIG. 1, a portable signalling unit of the present invention is shown. The unit comprises a terminal block 11 with a plurality of wire contacts 13 along an upper surface of the block. The wire contacts serve for terminating EKG leadwires 15. The wire contacts may be plugs or receptacles which receive corresponding jacks associated with the EKG leadwires. There are a total of fourteen wire contacts, including a right leg contact 19 and a left leg contact 17.

Similarly, there is a right arm contact 23, as well as a left arm contact 21. The left and right leg contacts, as well as the left and right arm contacts are segregated on the terminal block in positions corresponding to positions of the human body so that an operator can associate leadwires more readily. Each of the leadwires, such as left leg contact 17 has a corresponding trace 25 to the video display 27, at a position where the video display will show a graphic character corresponding with signals on the associated lead. Each of the top traces 29 extends from one of the upper wire contacts to a portion of the video display 27 where information associated with the corresponding leadwire will be displayed.

The terminal block 11 houses video drivers 31 which are similar to drivers for the display of an LCD watch. The video display 27 has a plurality of cells, each corresponding to one of the leadwires. A portion or the entirety of each cell is activated by a video driver in accord with information received through the transceiver 33. The transceiver has a transmit and a receive section. The receive section is connected to a decoder which receives information from a remote EKG apparatus and provides signals to the video drivers previously mentioned. The transmitter receives information from the wire contacts which it encodes and transmits to the remote EKG apparatus via a serial digital communication protocol. The transceiver can maintain simultaneous bidirectional communication with a host transceiver. On the transmit side, the transceiver includes a channel for each of the wire contacts, plus a channel for a signalling button 35 which may be a simple pushbutton switch.

Pushbutton 35 may be used to control the operation of the remote EKG host system. For example, the pushbutton may be used for telegraphically communicating over a communications channel the start or finish of an EKG measurement. The pushbutton 35 is located centrally on the terminal block 11 for easy manual access by an operator. The button push is indicated by a change of the information displayed on the LCD. Besides controlling operation of the remote EKG apparatus, pushbutton 35 may be used to control a local power supply 37. This supply may be a battery supply since the power requirements of the portable unit are very modest.

The signalling unit of the present invention communicates to a remote EKG master system by means of a radio frequency cable 39 which may be a coaxial transmission line or a multiconductor shielded cable. Because communication is at radio frequencies, it is not necessary to use a cable, but an optical signalling path may also be used. A laser diode or light emitting diode may be modulated with the information contained on all of the channels by means of a multiplexer. The host EKG apparatus may have a photodetector for receiving such information and a separate light source for transmitting return information. Other types of communication channels, such as radio links can also be used. However, the cable is simplest where the distance between the portable unit and the base EKG unit is not very far, i.e. within the same building.

Figure 2:
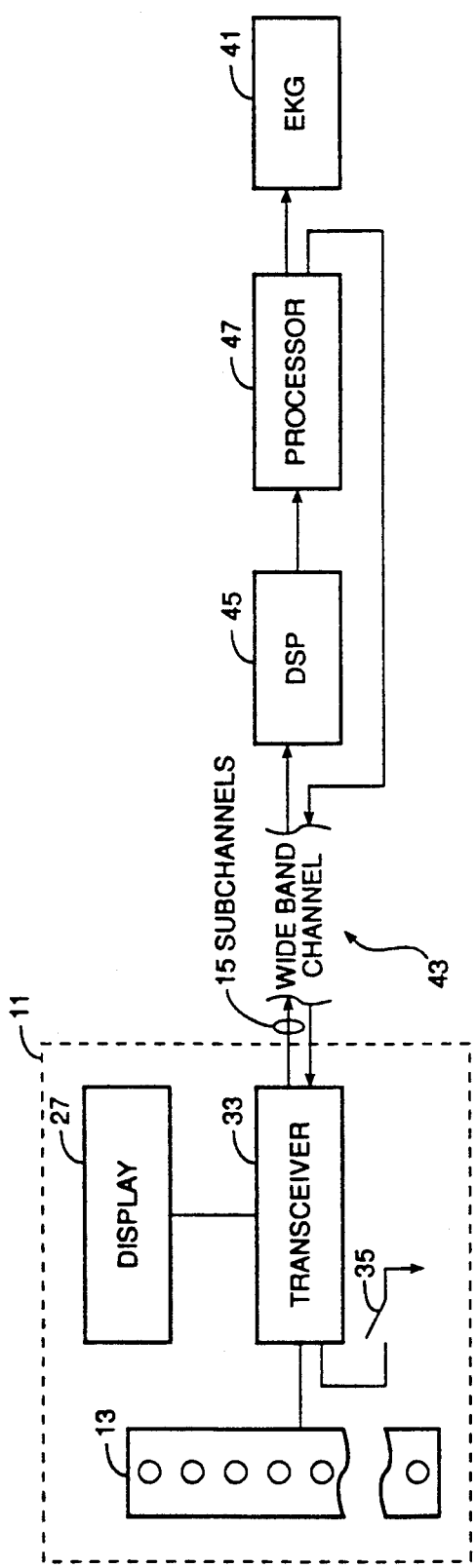
FIG. 2 is a schematic view of the electrical connection between a signalling unit of the present invention and the host EKG unit.

With reference to FIG. 2, the overall signal path to an EKG host may be seen. The terminal block 11 containing wire contacts 13, video display 27 and communications transceiver 33 is seen to be linked to a remote DSP 45 through a wide band radio frequency communications channel 43. By wide band is meant that the channel must have sufficient bandwidth to accommodate fourteen subchannels, each carrying information from an EKG leadwire connected to a patient, plus one subchannel for the button information.

As a front end to the EKG unit, a digital signal processor 45 receives information from the transmit side of transceiver 33. The processor evaluates incoming signals in a manner described more fully with reference to FIGS. 4–6 and then communicates with the general purpose processor 47 which creates bar graph information for transmission to display 27. Processor 47 is connected to the transmit side of the communications channel from the remote end and communicates with the receiver section of transceiver 33. The information which is received is decoded and sent to the video display 27 where noise amplitude is visually displayed in a manner to be described with reference to FIG. 7. Electrodes on/off status and alphanumeric messages are also displayed.

Figure 3:
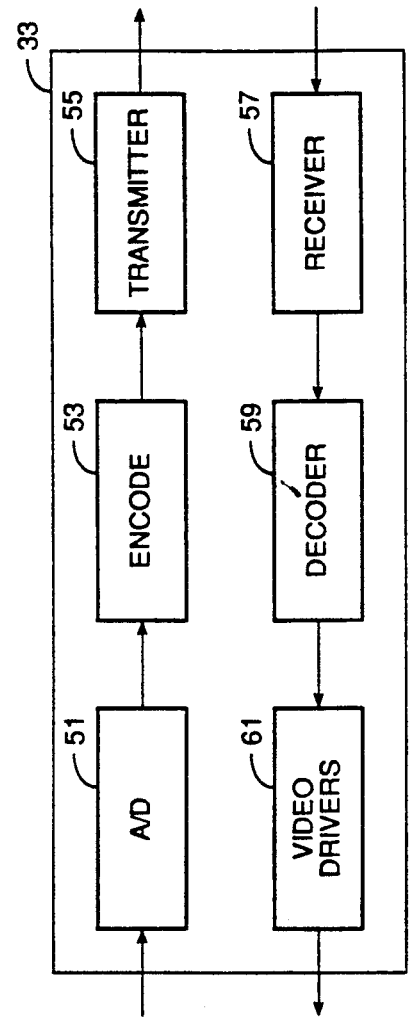
FIG. 3 is an electrical diagram of a transceiver which is a part of a portable signalling unit in accord with the present invention.

With reference to FIG. 3, the transceiver 33 is described. Each electrical lead which terminates in a wire contact providing a signal which is transmitted to an analog-to-digital converter 51. The converter transmits its signal to an encoder which places the information on its corresponding channel in the serial digital transmission protocol. The transmitter 55 then sends this data to the remote EKG apparatus via the wide band channel. The output from transmitter 55 is supplied to the wide band channel.

Receiver 57 receives a signal from the wide band channel which is decoded in decoder 59. The received signal contains an encoded indication of the amount of noise in a channel and this noise amplitude signal is appropriate for the video display drivers 61. One driver is associated with each cell of the video display as described below. Video drivers for LCD displays are well known. In this case, each cell is a miniature bit map so that blocks of pixels may be switched or alphanumeric characters may be displayed.

Figure 4:
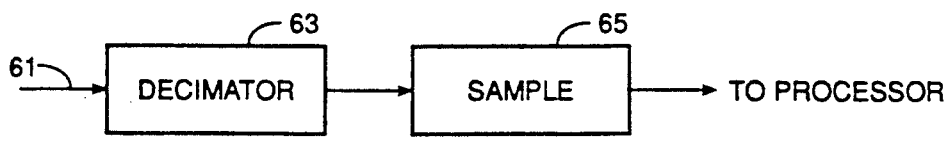
FIGS. 4-6 are block diagrams of electrical signal processing associated with the host EKG system.
Figure 5:
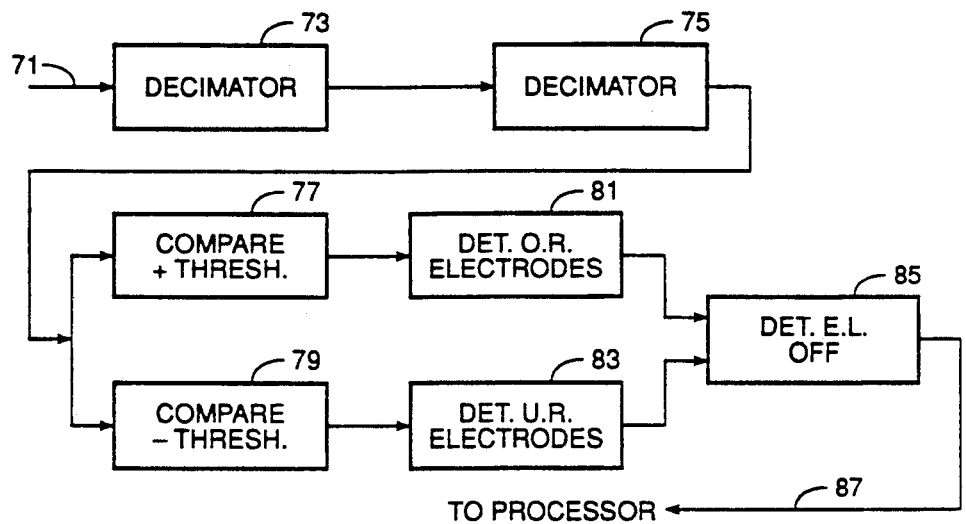
Figure 6:
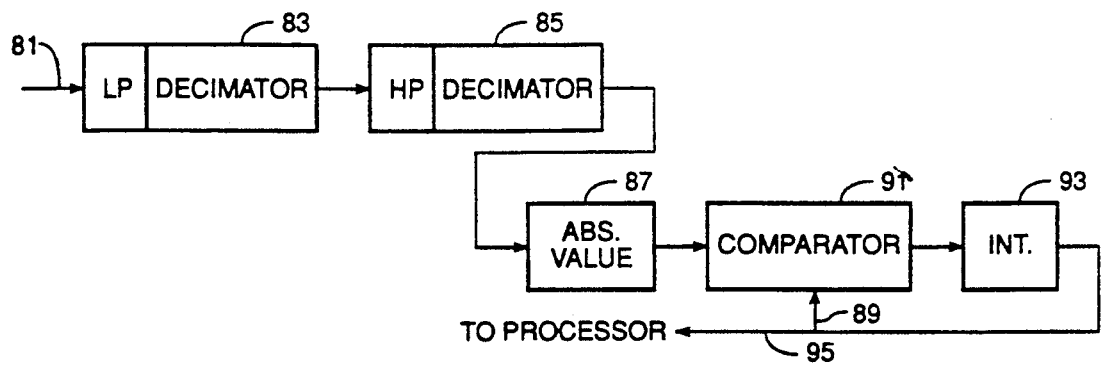

FIGS. 4–6 indicate the operation of the digital signal processor for different channels of information. FIG. 4 is related to the status of pushbutton 35. Line 61 in FIG. 4 represents an incoming channel with button status.

The signal is at 4 kHz before entering decimator 63 where the signal is reduced to 100 samples/second. These pulses are sampled within the general purpose processor, thereby determining button status information. The button status detection algorithm is indicated by block 65. This algorithm merely determines whether data registers where the button channel information is sent are in a high state or in a low state. One state indicates a button is down, the other that the button is up. The button signal is digitally debounced.

Figure 4A:
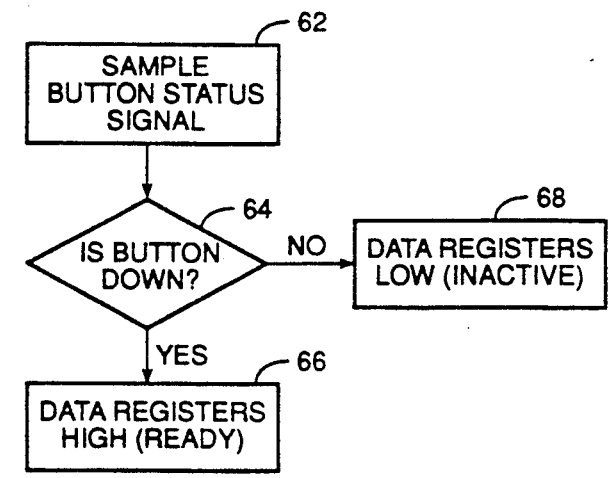

With reference to FIG. 4a, the button status signal is sampled by a general purpose processor, as indicated in block 62. If the button is down, a first signal will be detected, but if the button is up a second signal, or lack of signal, will be detected, as indicated in decision block 64. If the button is down, data registers are now set high or ready, as indicated by block 66 while if the button is up, data registers are set low, as indicated by block 68.

FIGS. 5 and 6 represent blocks associated with each of the electrode wire channels in the digital signal processor. In FIG. 5, such a channel is indicated by a line 71 carrying 4 kHz data to decimator 73 where the signal is reduced to a rate of 1 kHz data grouped in packets of 20 milliseconds. The incoming data is also filtered and transmitted to the second decimator 75 where the data is reduced to 100 samples/second data in packets of 20 milliseconds. These packets are then transmitted to comparators 77 and 79. Comparator 77 has a positive threshold voltage while comparator 79 has a negative threshold voltage. The digital signal processor then has an algorithm for determining from the comparators whether the signal is over the allowable range (O.R.), or in the case of block 83, whether the signal is under range (U.R.). An overrange reading results from a disconnected leadwire. An underrange reading results from either a disconnected leadwire or a disconnected limb leadwire. This determination is made by software within the digital signal processor and is indicated by block 85, with an output signal set along line 87 to the general purpose processor.

In FIG. 6, there is a diagram of noise determination within a channel. An incoming electrode channel signal 81 is transmitted to a first decimator 83 where the signal is reduced from 4 kHz to 1 kHz of data in packets of 20 milliseconds. Low pass filtering is also applied before the signal is transmitted to a second decimator 85 where the signal is further reduced to 500 Hz and sent through a high pass filter in packets of 20 milliseconds. The digital signal processor then computes the absolute value of the signal, indicated by block 87. Next, the digital signal processor computes for each sample at 500 samples/second whether the sample is greater than, less than or equal to the previous output, indicated by line 89. The output from this comparison operation in block 91 then undergoes an integration indicated in block 93. This becomes the output transmitted to the general purpose processor along line 95, as well as the feedback previously mentioned on line 89. The average amount of change in a signal is indicative of the amount of noise. Within the general purpose processor, the noise signal from each channel is plotted in a mapping operation which is indicated in FIG. 7.

Figure 7:
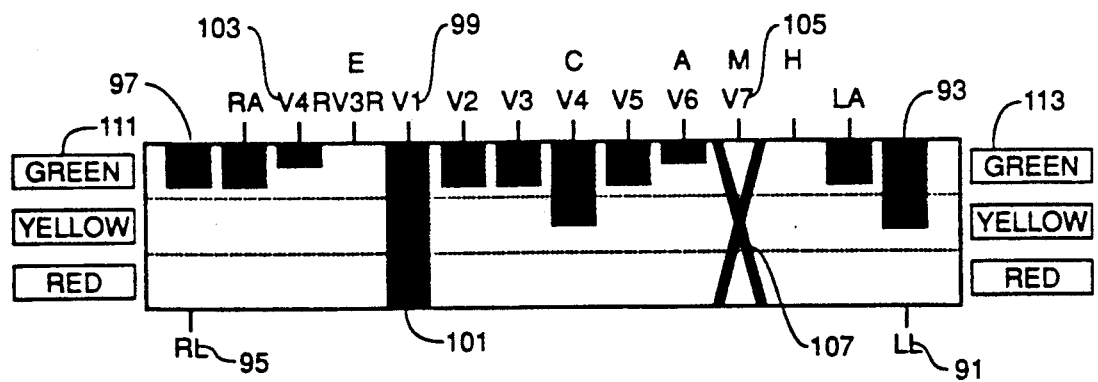
FIG. 7 is a diagram of a video display in the apparatus shown in FIG. 1.

FIG. 7 is the cell display in video display 27 of FIG. 1. However, a counterpart of the bit map exists in the memory of the general purpose processor 47 of FIG. 2. For each of the leadwire channels, there is an indication of the status of the corresponding electrode for example, in channel LL, 91, associated with the left leg there is a moderate amount of noise as shown by cell 93 which is dark in approximately two thirds of its vertical length. On the other hand, the channel RL, 95, associated with the right leg has a lesser amount of noise or no noise indicated by the block 97 which extends only one third of the length of the corresponding cell. Electrode V1, 99 has a block 101 extending entirely across the cell indicating an extremely noisy electrode which should be repositioned. On the other hand, the electrode V4, 103 indicates a not present electrode. A not present electrode is one for which a shorting plug is inserted. The cell corresponding to electrode V7, 105 has a ×107 in the cell. This indicates an electrode off condition and alerts an operator to take corrective action. There are seven heights of noise bars, where 1 level indicates little or no noise. Seven levels indicates a high amount of noise. At opposite ends of the video display or color marks 111 and 113 the top mark is green indicating that the top third of the display is a zone with acceptable limits of noise. Immediately below the green mark is a yellow zone indicating that noise is greater than the preferred amount, but still acceptable. The last zone is red and indicates unacceptable amounts of noise in a particular channel. The marks are painted at the opposite ends of the display or may be colored lamps. In FIG. 7 there is one vertical cell for each of the ten contacts at the top of terminal block 11 in FIG. 1, plus four cells for the arm and leg contacts. Of course, a user need not use all of the leadwires and this will be indicated by the X marks previously described. A blank mark indicates a not present electrode. This is one for which a shorting plug has been inserted in the connection.

We claim:

1. A portable unit for monitoring EKG functioning comprising,
    a terminal block having wire contact means connected to the block for terminating EKG leadwires from a subject to be connected to the leadwires,
    a signal transceiver housed in the block and communicating with said wire contact means, having means for encoding signals from the wire contact means for transmission to a remote EKG and having receiver means for decoding signals from a remote source associated with the EKG,
    a bidirectional communications channel connected to said signal transceiver on one end and having a remote second end connected to the remote source, the channel carrying signals in both directions therebetween,
    signal processor means connected to the EKG apparatus and to said remote second end of the communications channel for evaluating the quality of signals received from said transceiver.

2. The apparatus of claim 1 having a pushbutton means on said terminal block for telegraphically communicating with the signal processor means over said communications channel.

3. The apparatus of claim 1 having a video display means connected to said receiver means for displaying decoded signal quality information.

4. A portable unit for monitoring EKG functioning comprising,
    a video display including driver means for presenting information on the display,
    wire contact means proximate to the video display for terminating EKG leadwires from a subject to be connected to the leadwires,
    a signal transceiver means connected to the video display and connected to said wire contact means for sampling signals from said wire contact means and for encoding said sampled signals and having receiver means connected to said driver means for decoding signals from a remote source,
    a bidirectional communications channel connected to said signal transceiver on one end and having a remote second end,
    signal processor means connected to an EKG apparatus and to said remote second end of the communications channel for evaluating the quality of signals received from said transceiver and for returning to the transceiver signal quality evaluation information in said channel for display in said video display.

5. The apparatus of claim 4 wherein said video display is a one line LCD display.

6. The apparatus of claim 4 wherein said video display comprises a plurality of display blocks, each block having video driver means for displaying information independent of other blocks, there being a block corresponding to each leadwire or character in a text message.

7. The apparatus of claim 4 further comprising an on-off switch means proximate to the video display means and connected to the signal transceiver for manually signalling.

8. The apparatus of claim 4 wherein signals in each of said EKG leadwires is encoded in a subchannel, said bidirectional communications channel contains all of said subchannels.

9. The apparatus of claim 4 wherein said transceiver means for sampling signals and for encoding said sampled signals includes a transmitter means for transmitting at radio frequencies.

10. The apparatus of claim 4 wherein said signal processor means includes signal detection means for determining subject connection to said leadwires, signal comparison means for determining discrete levels of noise in said leadwires and driver means for generating an output signal corresponding to seven discrete levels of noise in said leadwires.

11. The apparatus of claim 4 further comprising a terminal block supporting the video display in the central position with visible traces between the wire contact means and spaced apart positions on the display.

* * * * *